(12) United States Patent
Cha et al.

(10) Patent No.: US 11,986,308 B2
(45) Date of Patent: May 21, 2024

(54) BIOSIGNAL MEASURING APPARATUS, METHOD FOR DETECTING SIGNAL PEAKS IN AN ELECTROCARDIOGRAM OF DETECTING AN EFFECTIVE PEAK USING THE COMPLEXITY VALUE AROUND THE PEAK IN THE WAVELET TRANSFORMED SIGNALS, AND A COMPUTER PROGRAM FOR PERFORMING THE METHODS

(71) Applicant: ATSENS CO., LTD., Gyeonggi-do (KR)

(72) Inventors: Kab Mun Cha, Seoul (KR); Jong Ook Jeong, Gyeonggi-do (KR)

(73) Assignee: ATSENS CO., LTD., Gyeonggi-Do (KR)

( * ) Notice: Subject to any disclaimer, the term of this patent is extended or adjusted under 35 U.S.C. 154(b) by 463 days.

(21) Appl. No.: 17/325,881

(22) Filed: May 20, 2021

(65) Prior Publication Data

US 2021/0369177 A1    Dec. 2, 2021

(30) Foreign Application Priority Data

Jun. 2, 2020    (KR) .................. 10-2020-0066696

(51) Int. Cl.
| | |
|---|---|
| *A61B 5/352* | (2021.01) |
| *A61B 5/00* | (2006.01) |
| *A61B 5/346* | (2021.01) |
| *G01R 23/16* | (2006.01) |
| *G16H 40/67* | (2018.01) |
| *G16H 50/70* | (2018.01) |
| *G06F 17/10* | (2006.01) |
| *G16H 50/20* | (2018.01) |

(52) U.S. Cl.
CPC .............. *A61B 5/352* (2021.01); *A61B 5/346* (2021.01); *A61B 5/726* (2013.01); *G01R 23/16* (2013.01); *G16H 40/67* (2018.01); *G16H 50/70* (2018.01); *G06F 17/10* (2013.01); *G16H 50/20* (2018.01)

(58) Field of Classification Search
CPC .......... A61B 5/436; A61B 5/352; A61B 5/726
See application file for complete search history.

(56) References Cited

U.S. PATENT DOCUMENTS

| | | | |
|---|---|---|---|
| 8,954,140 B2 * | 2/2015 | Mottaiyan ............ | A61B 5/7203 600/521 |
| 2002/0138014 A1 * | 9/2002 | Baura .................. | A61B 5/0295 600/526 |
| 2009/0192399 A1 | 7/2009 | Choi et al. | |

FOREIGN PATENT DOCUMENTS

| | | |
|---|---|---|
| KR | 1020060079444 A | 7/2006 |
| KR | 1020090081885 A | 7/2009 |
| KR | 1020140041327 A | 4/2014 |

OTHER PUBLICATIONS

Office Action issued in Korean counterpart KR Application No. 1020200066696, dated Jun. 29, 2021, 6 pages.

* cited by examiner

*Primary Examiner* — Michael W Kahelin
*Assistant Examiner* — Luke M Stanley
(74) *Attorney, Agent, or Firm* — Guntin & Gust, PLC; Miyoung Shin

(57) ABSTRACT

One or more embodiments relate to a bio-signal measurement apparatus and a bio-signal measurement method for detecting peaks and a computer program for executing the method. Sensed ECG signal is wavelet transformed into one or more levels, and an effective peak of a bio-signal is detected using a complexity value of a signal surrounding the peak in the converted signals.

7 Claims, 10 Drawing Sheets

BIOSIGNAL MEASURING APPARATUS, METHOD FOR DETECTING SIGNAL PEAKS IN AN ELECTROCARDIOGRAM OF DETECTING AN EFFECTIVE PEAK USING THE COMPLEXITY VALUE AROUND THE PEAK IN THE WAVELET TRANSFORMED SIGNALS, AND A COMPUTER PROGRAM FOR PERFORMING THE METHODS

CROSS-REFERENCE TO RELATED APPLICATION

This application is based on and claims priority under 35 U.S.C. § 119 to Korean Patent Application No. 10-2020-0066696, filed on Jun. 2, 2020, in the Korean Intellectual Property Office, the disclosure of which is incorporated by reference herein in its entirety.

BACKGROUND

1. Field

One or more embodiments relate to a bio-signal measurement apparatus and a bio-signal measurement method for detecting peaks and a computer program for executing the method. Sensed ECG signal is wavelet transformed into one or more levels, and an effective peak of a bio-signal is detected using a complexity value of a signal surrounding the peak in the converted signals.

2. Description of the Related Art

In a conventional stand-alone type or stationary electrocardiogram measuring device, a gap (distance) between electrodes attached to a user is large, and a user maintains a fixed posture to measure electrocardiogram signals of the user. Therefore, a change in a base line of a measured electrocardiogram signal is not significant, and the magnitude of a measured electrocardiogram signal is large.

In contrast, in a wearable patch-type electrocardiogram measurement device, a distance between electrodes is small, and a measured electrocardiogram signal is obtained when a user moves frequently. In an electrocardiogram signal measured in this way, in addition to general human body noises, various types of noises due to movements are inevitable. Also, the base line of an electrocardiogram signal measured in this way is not stable and varies significantly. Also, the magnitude of an electrocardiogram signal measured in this way is relatively small as compared to the size of an electrocardiogram signal measured by using an expensive stand-alone type or stationary electrocardiogram measuring device.

Therefore, it is difficult to detect an R-peak of an electrocardiogram signal by using a patch-type electrocardiogram measuring device.

SUMMARY

One or more embodiments provide a bio-signal measurement apparatus for wavelet transforming the sensed electrocardiogram signal into one or more level and for detecting a signal peak by using complexity values of signals around a peak, a method for detecting a signal effective peak of an electrocardiogram, and a computer program for executing the above method.

Additional aspects will be set forth in part in the description which follows and, in part, will be apparent from the description, or may be learned by practice of the presented embodiments of the disclosure.

According to one or more embodiments, a bio-signal measurement apparatus includes a bio-signal sensing circuit configured to sense an electrocardiogram signal using an electrode attached to a body; a pre-processor configured to pre-process the electrocardiogram signal based on a magnitude value of each signal; a first transformer configured to convert the electrocardiogram signal to first transform signal by first-level wavelet transforming; a second transformer configured to convert the electrocardiogram signal to second transform signal by second-level wavelet transforming; a candidate peak detector configured to detect first candidate peaks based on a magnitude of a first transform signal and detect second candidate peaks based on a magnitude of a second transform signal; a peak merger configured to define windows as time periods in the pre-processed electrocardiogram signal and calculate average values of time values of the first candidate peaks and the second candidate peaks included in the windows as average peak time values of the windows; and an effective peak detector configured to calculate complexity values for time periods including the average peak time values with respect to the first transform signal and the second transform signal, determine peak occurring time values based on complexity values with respect to the first transform signal and complexity values with respect to the second transform signal, and detect effective peaks in the electrocardiogram signal by using the peak occurring time values.

In at least one variant, the effective peak detector may define a first time period including a first average peak time value from among the average peak time values, calculate a first complexity value with respect to the first transform signal and a second complexity value with respect to the second transform signal within the first time period, and, when both the first complexity value and the second complexity value exceed a pre-set critical complexity level, determine the first average peak time value included in the first time period as a peak occurring time value.

In one variant, the pre-set critical complexity level may be a value determined based on complexity values of a pre-processed electrocardiogram signal within time periods including R peaks designated in the electrocardiogram signal. The complexity value may be a value calculated by applying a Shannon entropy algorithm to the signals.

In further one variant, the peak merger may be implemented so as not to calculate an average peak time value corresponding to a first window, which is defined as a time period in a pre-processed electrocardiogram signal, when there are no candidate peaks included in the first window.

According to one or more embodiments, a method of detecting a signal peak, the method includes sensing, by a bio-signal measurement apparatus, an electrocardiogram signal by using an electrode attached to a body; pre-processing, by the bio-signal measurement apparatus, the electrocardiogram signal based on a size of data; generating a first transform signal by first-level wavelet transforming the electrocardiogram signal; generating a second transform signal by second-level wavelet transforming the electrocardiogram signal; detecting first candidate peaks constituting peaks based on a size of data with respect to the first transform signal and detecting second candidate peaks constituting peaks based on a size of data with respect to the second transform signal; defining windows as time periods in the pre-processed electrocardiogram signal and calculating average values of time values of the first candidate peaks and the second candidate peaks included in the windows as average peak time values of the windows; and calculating complexity values for time periods including the average peak time values with respect to the first transform signal and the second transform signal, determining peak occurring time values based on complexity values with respect to the first transform signal and complexity values with respect to the second transform signal, and detecting effective peaks in the electrocardiogram signal by using the peak occurring time values.

In at least one variant, in the process of detecting effective peaks, a first time period including a first average peak time value from among the average peak time values may be defined and a first complexity value with respect to the first filtering signal and a second complexity value with respect to the second filtering signal within the first time period may be calculated, and, when both the first complexity value and the second complexity value exceed a pre-set critical complexity level, the first average peak time value included in the first time period may be determined as a peak occurring time value.

In one variant, the pre-set critical complexity level may be a value determined based on complexity values of a pre-processed electrocardiogram signal within time periods including R peaks designated in measured electrocardiogram signals. The complexity value may be a value calculated by applying a Shannon entropy algorithm to the signals within a time period. The calculating of the average peak time values may be implemented so as not to calculate an average peak time value corresponding to a first window, which is defined as a time period in the pre-processed electrocardiogram signal, when there is no candidate peaks included in the first window.

According to one or more embodiments, there is provided a computer program stored in a computer-readable storage medium to execute any one of methods by using a computer.

According to one or more embodiments, there is provided another method for implementing one or more embodiments, another system for implementing one or more embodiments, and a computer-readable recording medium having recorded thereon a computer program for executing the method.

Other aspects, features, and advantages will become apparent from the following drawings, claims, and detailed description of the invention.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
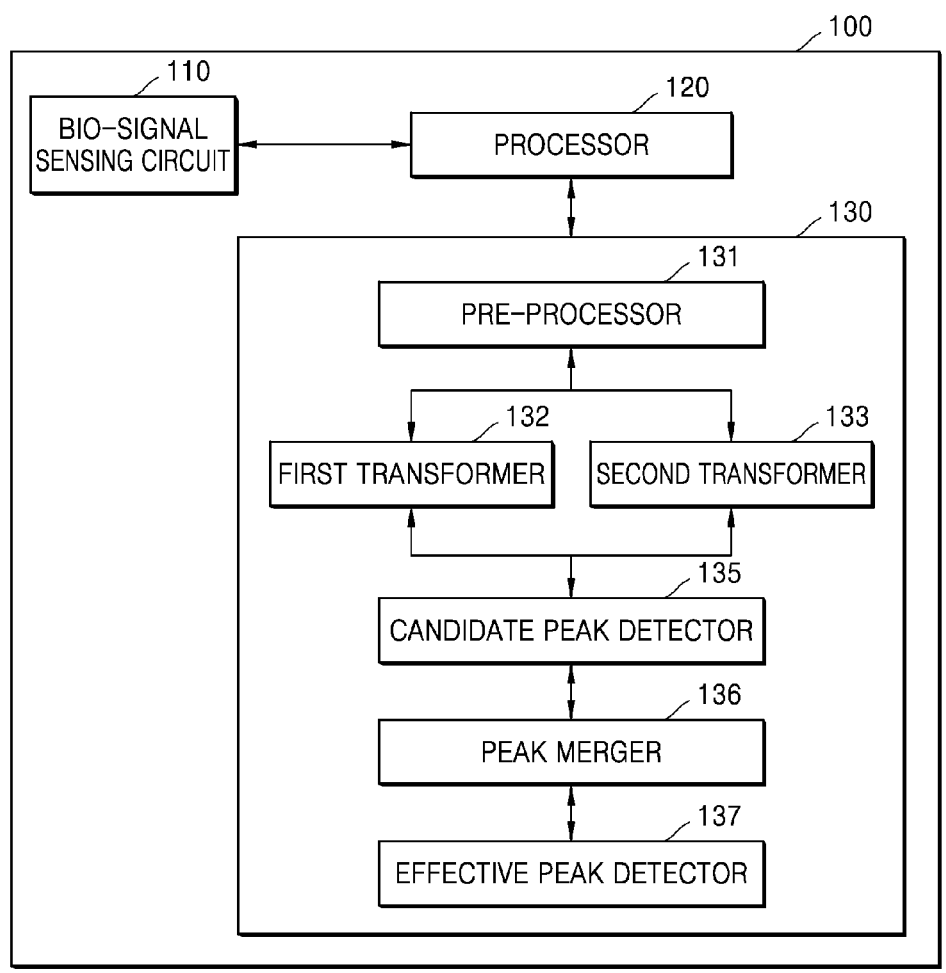
FIG. 1 is a block diagram of a bio-signal measurement apparatus 100 according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the configuration and operation of the present disclosure will be described in detail with reference to one or more embodiments shown in the accompanying drawings.

The present disclosure may include various embodiments and modifications, and embodiments thereof will be illustrated in the drawings and will be described herein in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

Reference will now be made in detail to embodiments, examples of which are illustrated in the accompanying drawings. In the drawings, the same elements are denoted by the same reference numerals, and a repeated explanation thereof will not be given.

It will be understood that although the terms "first", "second", etc. may be used herein to describe various elements, these elements should not be limited by these terms. These elements are only used to distinguish one element from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of elements in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

Figure 2:
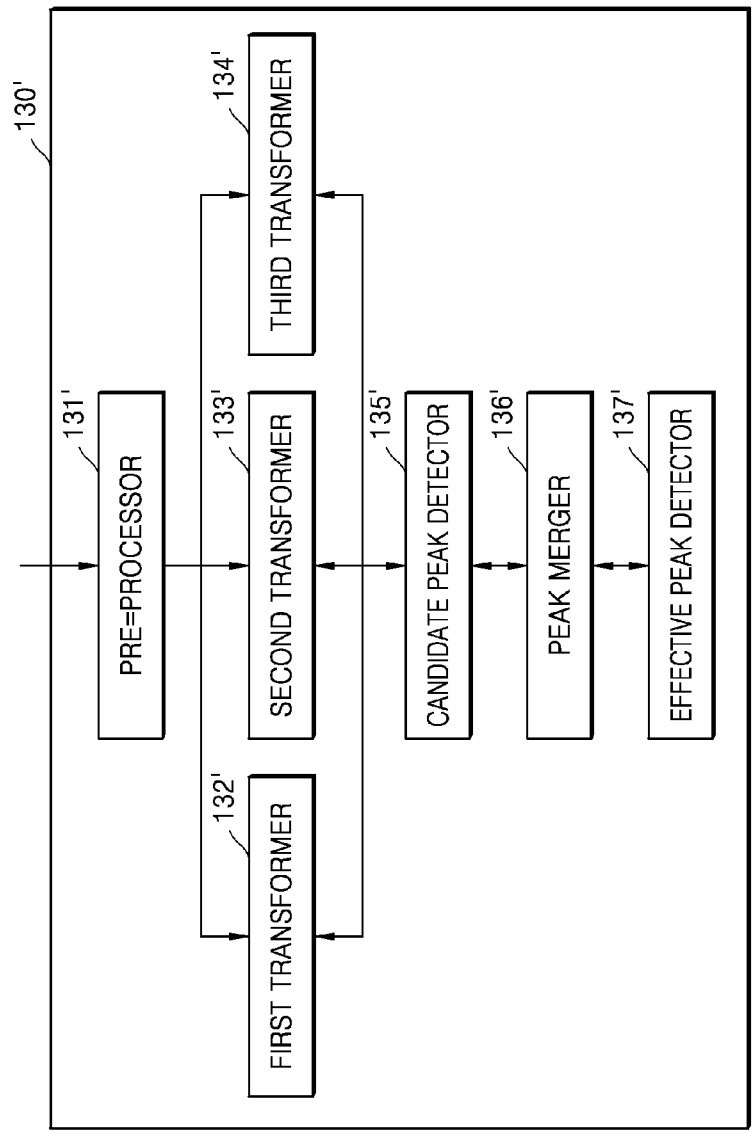
FIG. 2 is a block diagram of a bio-signal measurement apparatus 100' according to one or more embodiments.

FIG. 1 is a block diagram of a bio-signal measurement apparatus 100 according to one or more embodiments, and FIG. 2 is a block diagram of a bio-signal measurement apparatus 100' according to one or more embodiments.

The bio-signal measurement apparatus 100 includes a bio-signal sensing circuit 110, a pre-processor 131, a first transformer 132, a second filtering unit 133, a candidate peak detector 135, a peak merger 136, and an effective peak detector 137. At least one of the pre-processor 131, the first transformer 132, the second transformer 133, the candidate peak detector 135, the peak merger 136, and the effective peak detector 137 may be implemented as a hardware component. At least one of the pre-processor 131, the first transformer 132, the second transformer 133, the candidate peak detector 135, the peak merger 136, and the effective peak detector 137 may be implemented as a software component and may be executed by a separately provided processor. The bio-signal sensing circuit 110, the pre-processor 131, the first transformer 132, the second transformer 133, the candidate peak detector 135, the peak merger 136, and the effective peak detector 137 may be provided and implemented within a single device or may be provided in two or more devices.

The bio-signal measurement apparatus 100 may process a bio-signal sensed through the bio-signal sensing circuit 110. The bio-signal sensing circuit 110 may be attached to a user's body invasively or non-invasively and sense the user's bio-signals. The bio-signal sensing circuit 110 may obtain an electrocardiogram signal, which indicates an electrical change according to a heartbeat obtained from an electrode. The bio-signal sensing circuit 110 may include a measurement electrode for obtaining an electrocardiogram signal and an analog-digital (AD) transformer for transforming an analog electrocardiogram signal measured by the measurement electrode into digital electrocardiogram data. The bio-signal sensing circuit 110 may further include an amplifier for amplifying an electrocardiogram signal.

The bio-signal measurement apparatus 100 may include the pre-processor 131 that pre-processes a bio-signal such as an electrocardiogram signal based on the size of data, the first transformer 132 and the second transformer 133 that wavelet transform the bio-signal into predetermined orders, the candidate peak detector 135 for detecting candidate peaks included in transformed signals, the peak merger 136, and the effective peak detector 137.

The pre-processor 131 may pre-process an electrocardiogram signal based on the size of data. The pre-processor 131 may preprocess an electrocardiogram signal by transforming the electrocardiogram signal into an absolute value of each piece of data, but is not limited thereto.

The pre-processor 131 may provide the preprocessed electrocardiogram signal to first transform signal by first-level wavelet transforming through the first transformer 132 and provide the processed electrocardiogram signal to second transform signal by second-level wavelet transforming through the second transformer 133. Here, it is described that a frequency transformation is used for convenience of explanation, but it is obvious that various other transformation methods (e.g., a wavelet transformation, a Hilbert transformation, etc.) may be used. The first level transformed in the first transformer 132 and the second level transformed in the second transformer 133 may be set as a combination of levels having a higher hit rate for detecting an effective peak. The first level transformed in the first transformer 132 and the second level transformed in the second transformer 133 may be changed as an effective peak detection process is continuously performed.

The candidate peak detector 135 uses first candidate peaks included in a first transform signal that is wavelet transformed by the first transformer. The candidate peak detector 135 use also second candidate peaks included in a second transform signal that is wavelet transformed by the second transformer. First and second candidate peaks may be determined based on the magnitude of a signal. In detail, when a size value of first data is compared with a size value of second data measured at a preceding time and a size value of third data measured at a later time and the size value of the first data is greater than the size value of the second data and the size value of the third data, the first data may be detected as a candidate peak. The peak merger 136 calculates average peak time values of first candidate peaks of a first transform signal and second candidate peaks of a second transform signal by using windows defined as a time period. Here, a window may be set to have a width of a pre-set unit time. Here, the width (size) of the unit time may be determined based on a heart rate or an R-R interval of a user.

The peak merger 136 may merge the first candidate peaks of the first transform signal with the second candidate peaks of the second transform signal into one data and calculate an average value of time values of the first candidate peaks and the second candidate peaks in a window having a pre-set size based on a time value as an average time value. For example, when there are a candidate peak A and a candidate peak B in a first window, a time value of the candidate peak A and a time value of the candidate peak A may be calculated as an average peak time value. When there is no candidate peak in the first window, the average peak time value corresponding to the first window is recorded as nope (no existing) and is not calculated.

In the above-stated manner, the peak merger 136 may move a window of a predetermined size along the x-axis (time-axis) and calculate average peak time values based on first candidate peaks and second candidate peaks in the window.

The effective peak detector 137 calculates complexity values for time periods including average peak time values for each time period for the first transform signal and the second transform signal and detects effective peak points based on the complexity values for the first transform signal and the complexity values for the second transform signal. For example, when a complexity value for the first transform signal and a complexity value for the second transform signal with respect to a first average peak time value in a window of the first time period are equal to or greater than a pre-set critical complexity level, a point corresponding to the first average peak time value may be detected as an effective peak point. In this regard, effective peak points may be detected by using complexity values for average peak time values in windows throughout an entire time period.

Here, the complexity value may be calculated by using a complexity calculation algorithm such as the Shannon entropy. However, one or more embodiments are not limited thereto, and the complexity value may be calculated by using various methods such as Kolmogorov, monotone, prefix, and decision.

Here, the complexity value may be determined based on a frequency of occurrence for each size range of measured values of measured bio-signal data. Measured values of signals may be divided into multiple magnitude bins based on magnitudes of the signals. According to this, a first occurrence frequency may be calculated by extracting data (point, point, point) of signals included in a first magnitude bin. A high frequency of occurrence of one magnitude bin may indicate that signals (data) are generated in a similar pattern, and a low frequency of occurrence in each magnitude bin may indicate that signals have an irregular pattern, that is, a complex shape.

In other words, a complexity value may be calculated according to Equation 1 below by defining magnitude bins generated based on values obtained by measuring signals and calculating a frequency of occurrence of data points in each magnitude bin.

$$SE = -\sum_{m=1}^{M} p(m) \log_2 p(m) \quad \text{[Equation 1]}$$

Here, M denotes a size value of a magnitude bin of a signal, and p(m) denotes a function of a probability of occurrence of a signal in each bin period. For example, when m is 1, p(m) may represent a ratio between a total number L of data points and a number N of data points corresponding to m=1.

$$p(m) = \frac{N}{L}$$

In another embodiment, a complexity value may be calculated by using a turning point ratio (TPR). In this case, when the number of turning points per unit time is large, the complexity value may be high. When the number of turning points per unit time is small, the complexity value may be low. The TPR may be a value indicating a ratio of a location of a turning point indicating a change in magnitude of two adjacent pieces of data at a particular time point with respect to the total data length. Here, the turning point refers to a point at which a tangent of a signal is 0, that is, a point at which a direction of data values is changed. The complexity value may be calculated according to Equation 2.

$$TPR = \frac{N((x_i - x_{i-1})(x_i - x_{i+1}) > 0)}{L} \quad \text{[Equation 2]}$$

Here, N(x) denotes the number of pieces of data satisfying an x condition, and L denotes a size of a data section. $(N((x_i-x_{i-1})(x_i-x_{i+1})>0))$ denotes the number of points that are $(x_i-x_{i-1})(x_i-x_{i+1})>0$ in a period L, that is, the number of turning points.

The effective peak detector 137 determines a first time period of a window including a first average peak time value, calculates a first complexity value of a first transform signal for the first time period of the window, calculates a second complexity value of a second transform signal for the first time period, and, when it is determined that the first complexity value and the second complexity value exceed a pre-set critical complexity level, determines the first peak time value as a peak occurring time value in an electrocardiogram signal, which is a bio-signal. The effective peak detector 137 may detect peak occurring time values corresponding to peaks of an actual electrocardiogram signal in time periods through the above-stated process.

When it is determined that at least one of the first complexity value and the second complexity value does not exceed the pre-set critical complexity level, the first peak time value does not become a peak occurring time value.

The effective peak detector 137 may detect effective peaks in an electrocardiogram signal by using peak occurring time values. Accordingly, effective peaks useful for predicting a heart condition of an object may be accurately detected.

In the present specification, the pre-set critical complexity level, which is a criterion for selecting a peak occurring time value, is determined through a machine learning model that uses complexity values of time periods including peaks as input data and validity of the peaks as output data. However, one or more embodiments are not limited thereto, and the pre-set critical complexity level may be determined by using various neural networks, statistical techniques, etc.

In order to detect effective peaks in an electrocardiogram signal, effective peak occurring time values in the electrocardiogram signal may be detected by using signals wavelet transformed through a first transformer, a second transformer, and a third transform unit as shown in FIG. 2. The bio-signal measurement apparatus 100' of FIG. 2 may include a bio-signal sensing circuit 110', a pre-processor 131', a first transformer 132', a second transformer 133', and a third transform unit 134'. Because the bio-signal sensing circuit 110' is the same as the bio-signal sensing circuit 110, detailed descriptions thereof are omitted.

At least one of the pre-processor 131', the first transformer 132', the second transformer 133', the third transform unit 134', the candidate peak detector 135', the peak merger 136', and the effective peak detector 137' may be implemented as a hardware component. At least one of the pre-processor 131', the first transformer 132', the second transformer 133', the third transform unit 134', the candidate peak detector 135', the peak merger 136', and the effective peak detector 137' may be implemented as a software component and may be executed by a separately provided processor. The pre-processor 131', the first transformer 132', the second transformer 133', the third transform unit 134', the candidate peak detector 135', the peak merger 136', and the effective peak detector 137' may be implemented within one device or may be implemented in two or more devices. The pre-processor 131', the first transformer 132', the second transformer 133', the third transform unit 134', the candidate peak detector 135', the peak merger 136', and the effective peak detector 137' may be implemented as a remote device and receive and process bio-signals from the bio-signal sensing circuit 110'.

The preprocessor 131' may pre-process the electrocardiogram signal based on a data size value. The preprocessor 131' may preprocess the electrocardiogram signal by converting it into an absolute value of each data.

The first converter 132' may wavelet transform the pre-processed electrocardiogram signal into a first dimension. The second converter 133' may convert the preprocessed electrocardiogram signal into a second dimension wavelet. The third converter 134' may wavelet transform the pre-processed electrocardiogram signal into a third dimension.

Here, the wavelet transform may be replaced or replaced with another frequency transform method.

The candidate peak detector 134' detects first candidate peaks included in a first transformed signal transformed by the first transformer 131', second candidate peaks included in a second transformed signal transformed by the second transformer 132', and third candidate peaks included in a third transformed signal transformed by the third transformer 133'. The candidate peak detector 135' may generate first candidate peaks, second candidate peaks, and third candidate peaks as one integrated data.

The peak merger 136' calculates average peak time values of the first candidate peaks of the first transformed signal, the second candidate peaks of the second transformed signal, and the third candidate peaks of the third transformed signal by using windows defined as time periods. At least two candidate peaks among a 1-1 candidate peak, a 1-2 candidate peak, and a 1-3 candidate peak may be included in one transformed signal. For example, an average of time values of a 1-1 candidate peak, a 1-2 candidate peak, and a 1-3 candidate peak included in a first window defined as a first time period may be calculated and set as an average peak time value. The 1-1 candidate peak, the 1-2 candidate peak, and the 1-3 candidate peak may belong to at least one of the first candidate peaks, the second candidate peaks, and the third candidate peaks. The 1-1 candidate peak, the 1-2 candidate peak, and the 1-3 candidate peak may be included in different transformed signals, respectively. The 1-1 candidate peak and the 1-2 candidate peak may be included in the first filtering signal. Alternatively, the 1-1 candidate peak, the 1-2 candidate peak, and the 1-3 candidate peak may be included in the first transformed signal.

The peak merger 135' may merge the first candidate peaks, the second candidate peaks, and the third candidate peaks based on time values and, after merging, calculate an average of time values of the first candidate peaks, the second candidate peaks, and the third candidate peaks as an average peak time value by using a window having a set time period (size). The number of candidate peaks included in the window may be 0 or 3 or more. For example, when there are an A candidate peak, a B candidate peak, a C candidate peak, and a D candidate peak in the first window, an average value of time values of A to D candidate peaks may be transformed into an average peak time value. When there is no candidate peak in the first window, the average peak time value corresponding to the first window is recorded as nope and is not calculated. The peak merger 136' may first detect the number of candidate peaks included in the window, and calculate average values of time values of the candidate peaks based on the number of candidate peaks.

In the above-stated manner, the peak merger 136' may move a window having a pre-set size along the x-axis with respect to data including the first candidate peaks and the second candidate peaks and calculate average peak time values of the first candidate peaks and the second candidate peaks.

The effective peak detector 137' calculates complexity values for time periods including peak time values from first to third transformed signals and detects peak occurring time values based on the calculated complexity values, respectively. Here, the complexity value may be calculated by using a complexity calculation algorithm such as Shannon entropy. The complexity value may be calculated using one of Equations 1 to 2 above, but is not limited thereto and may be calculated using various equations.

The effective peak detector 137' determines a first time period including a first average peak time value, calculates a first complexity value of a first transformed signal for a first time period, a second complexity value of a second transformed signal for the first time period, and a third complexity value of a third transformed signal for the first time period, and, when it is detected that the first complexity value, the second complexity value, and the third complexity value exceed a pre-set critical complexity level, determines the first peak time value as a peak occurring time value. The effective peak detector 137' may detect effective peaks based on peak occurring time values calculated through the above-stated process. When it is determined that at least one of the first complexity value, the second complexity value, and the third complexity value does not exceed the pre-set critical complexity level, the first peak time value does not become a peak occurring time value.

The effective peak detector 137' determines windows defined as time intervals based on the average peak time values calculated using the effective peaks included in the converted signals, and calculates the complexity values of the converted signals within the windows. The peak occurrence time value can be determined on the basis. That is, the effective peak detector 137' may calculate a peak occurrence time value corresponding to the peak in the electrocardiogram signal based on the complexity values in the converted signals among average peak time values.

Figure 3:
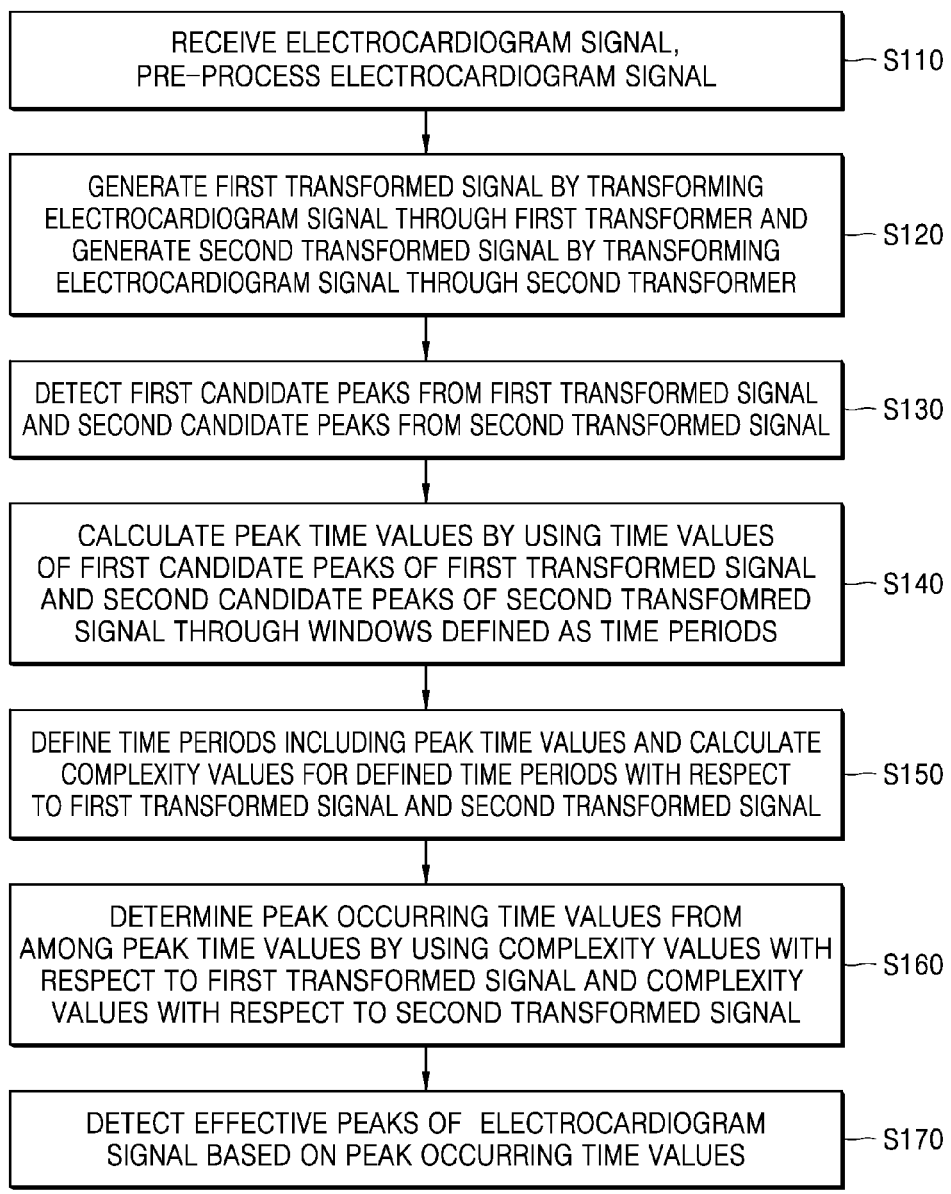
FIG. 3 is a flowchart of a method of detecting a signal peak according to first embodiment.
Figure 4:
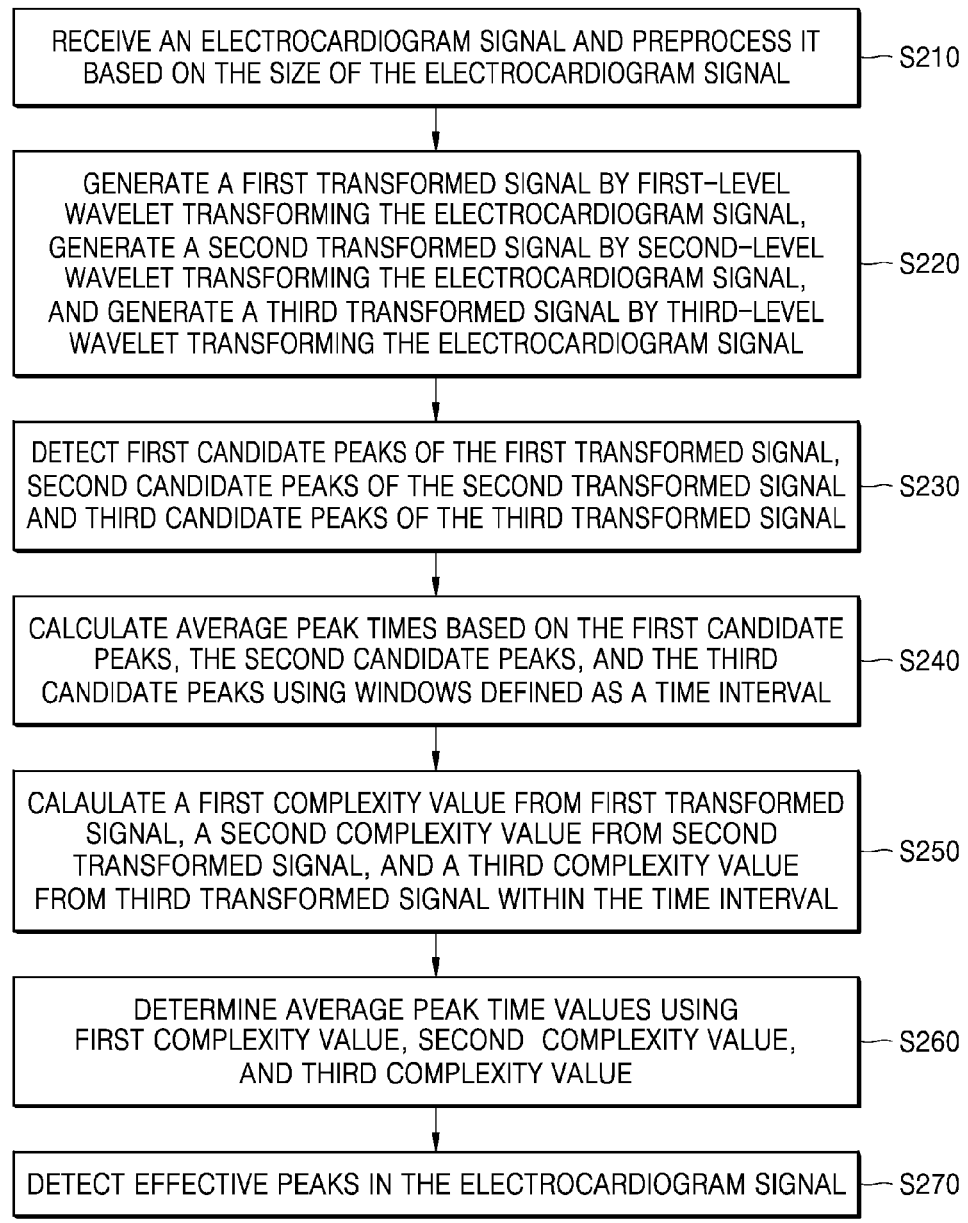
FIG. 4 is a flowchart of a method of detecting a signal peak according to second embodiment.

FIG. 3 is a flowchart of a method of detecting a signal peak according to one or more embodiments of the present disclosure.

In operation S110, the bio-signal measurement apparatus 100 receives an electrocardiogram signal from a sensing circuit. In operation S110, the bio-signal measurement apparatus 100 may pre-process the electrocardiogram signal based on the size of the electrocardiogram signal. The bio-signal measurement apparatus 100 may preprocess the electrocardiogram signal by converting it into an absolute value of each data. In operation S120, the bio-signal measurement apparatus 100 converts the preprocessed electrocardiogram signal to a first level through the first conversion unit 132, and converts the preprocessed electrocardiogram signal to a second dimension through the second conversion unit 133. The first level transformed by the first transformer 132 and the second level transformed by the second transformer 133 may be set as a combination of levels having a higher hit rate for detecting an effective peak. The first level transformed by the first transformer 132 and the second level transformed by the second transformer 133 are changed to a value effective for detecting the effective peak as the process of detecting the effective peak is continuously performed.

In operation S130, the bio-signal measurement apparatus 100 detects first candidate peaks included in a first filtering signal filtered by the first transformer. The bio-signal measurement apparatus 100 detects second candidate peaks included in a second transformed signal filtered by the second transformer.

The first and second candidate peaks may be determined based on the size of the signal. Compared with the size value, when the size value of the first data is larger than the size value of the second data and the size value of the third data, the first data may be detected as a candidate peak.

In operation S140, the bio-signal measurement apparatus 100 calculates average peak time values of the first candidate peaks of the first transformed signal and the second candidate peaks of the second transformed signal by using windows defined as time periods. Here, a window may be set to have a width of a pre-set unit time. Here, the width (size) of the unit time may be determined based on a heart rate or an R-R interval of a user.

The bio-signal measurement apparatus 100 merges the first candidate peaks and the second candidate peaks into one data, and from the merged data, the average value of the time values of the first candidate peaks and the second candidate peaks is an average peak time value. It can be calculated as the first candidate peaks and the second candidate peaks may exist in a window having a predetermined size based on a time value. When there is no candidate peak in a set window, the average peak time value corresponding to the first window is recorded as none and is not calculated.

The bio-signal measurement apparatus 100 may move a window having a pre-set size along the x-axis with respect to data including the first candidate peaks and the second candidate peaks and calculate average peak time values.

In operation S160, the bio-signal measurement apparatus 100 calculates complexity values for time periods including the average peak time values with respect to a first transformed signal and a second transformed signal and detects effective peak points based on the complexity values for the first transformed signal and the complexity values for the second transformed signal. The effective peak points may be a point corresponding to the peak occurrence time value by determining peak occurrence time values among average peak time values. Here, the complexity value may be calculated by using a complexity calculation algorithm such as Shannon entropy.

The complexity value may be determined based on a frequency of occurrence for each size range of measured values of measured bio-signal data. Measured values of signals may be divided into multiple magnitude bins based on magnitudes of the signals. According to this, a first occurrence frequency may be calculated by extracting data (point, point, point) of signals included in a first magnitude bin. A high frequency of occurrence of one magnitude bin may indicate that signals (data) are generated in a similar pattern, and a low frequency of occurrence in each magnitude bin may indicate that signals have an irregular pattern, that is, a complex shape.

In other words, a complexity value may be calculated according to Equation 1 below by defining magnitude bins generated based on values obtained by measuring signals and calculating a frequency of occurrence of data points in each magnitude bin.

In another embodiment, a complexity value may be calculated by using a TPR. In this case, when the number of turning points per unit time is large, the complexity value may be high. When the number of turning points per unit time is small, the complexity value may be low. The TPR may be a value indicating a ratio of a location of a turning point indicating a change in magnitude of two adjacent pieces of data at a particular time point with respect to the total data length. Here, the turning point refers to a point at which a tangent of a signal is 0, that is, a point at which a direction of data values is changed. The complexity value may be calculated according to Equation 2.

The bio-signal measurement apparatus 100 determines a first time period a window of including a first average peak time value, calculates a first complexity value of a first transformed signal for the first time period, calculates a second complexity value of a second transformed signal for the first time period, and, when it is determined that the first complexity value and the second complexity value exceed a pre-set critical complexity level, determines the first peak time value as a peak occurring time value on the electrocardiogram signal. The bio-signal measurement apparatus 100 may detect actual peak occurring time values on the electrocardiogram signal in time periods through the above-stated process. If it is detected that at least one of the first complexity value and the second complexity value does not exceed a preset threshold complexity level, the first peak time value does not become a peak occurrence time value.

In operation S170, the bio-signal measurement apparatus 100 may detect effective peaks in an electrocardiogram signal by using peak occurring time values.

In S210, the bio-signal measurement apparatus 100' receives an electrocardiogram signal and preprocesses it based on the size of the electrocardiogram signal.

In S220, the bio-signal measurement apparatus 100' generate a first transformed signal by first level wavelet transforming the electrocardiogram signal, generate a second transformed signal by second level wavelet transforming the electrocardiogram signal, and generate a third transformed signal by third level wavelet transforming the electrocardiogram signal.

In S230, the bio-signal measurement apparatus 100' may detect candidate peaks that form a peak corresponding to adjacent signals based on the size of the signal.

In S240, the bio-signal measurement apparatus 100' uses windows defined as a time interval to determine first candidate peaks of the first transformed signal, second candidate peaks of the second transformed signal, and third candidate peaks of the third transformed signal. Average peak time values of candidate peaks are calculated. The bio-signal measurement apparatus 100' merges the first candidate peaks, the second candidate peaks, and the third candidate peaks based on a time value, and after merging, using a window having a predetermined time interval (size, length). An average value of time values of the first candidate peak, the second candidate peak, and the third candidate peak may be calculated as an average peak time value.

In S250, the bio-signal measurement apparatus 100' defines time intervals including average peak time values, and calculates a complexity value for the defined time interval from the first transformed signal, the second transformed signal, and the third transformed signal. The complexity value may be calculated using one of Equations 1 to 3 above, but is not limited thereto and may be calculated using various equations.

In S260, the bio-signal measurement apparatus 100' uses the first complexity value in the first transformed signal, the second complexity value in the second transformed signal, and the third complexity value in the third transformed signal to calculate average peak time values. Among them, peak occurrence time values can be determined. When it is detected that the first complexity value, the second complexity value, and the third complexity value exceed a preset threshold complexity level, the bio-signal measurement apparatus 100' detects the first peak time value as a peak occurrence time value.

In S270, the bio-signal measurement apparatus 100' may detect effective peaks in the electrocardiogram signal based on peak occurrence time values.

Figure 5A:
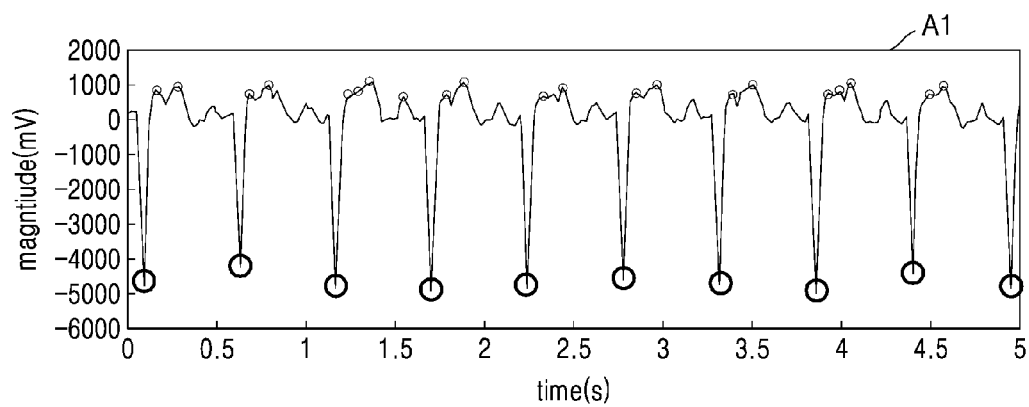
FIG. 5A is an exemplary diagram of an electrocardiogram signal.
Figure 5B:
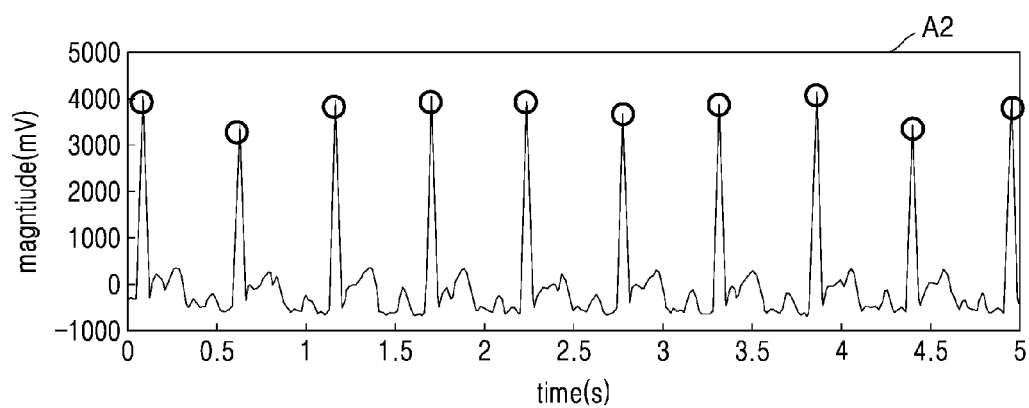
FIG. 5B is a diagram showing examples of a signal processed by a preprocessor according to one or more embodiments.

FIG. 5A is an exemplary diagram of an electrocardiogram signal. FIG. 5B is a diagram showing examples of a signal processed by a preprocessor according to one or more embodiments.

As illustrated in FIG. 5A and FIG. 5B, the biosignal measurement apparatus 100 may generate a signal A2 obtained by converting the electrocardiogram signal A1 based on the signal size.

The transformed signal A2 may be a signal generated by converting the size of the electrocardiogram signal A1 into an absolute value.

Figure 6A:
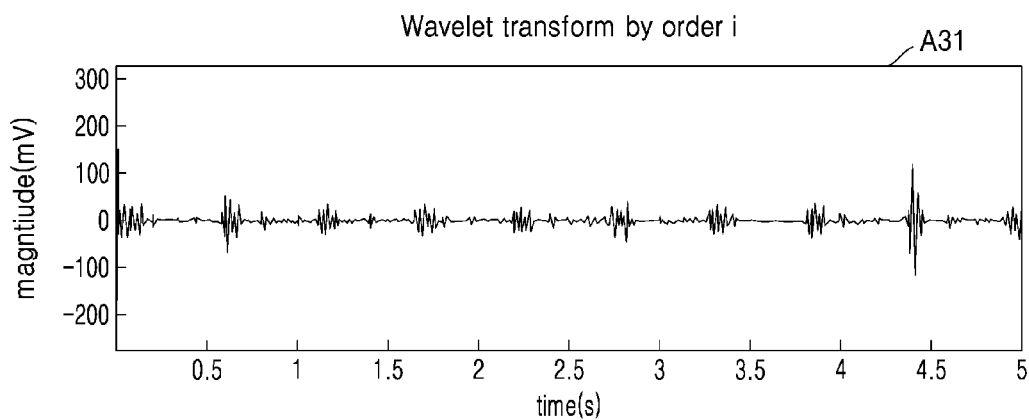
FIG. 6A is a diagram of a first transformed signal in an i-level according to one or more embodiments.
Figure 6B:
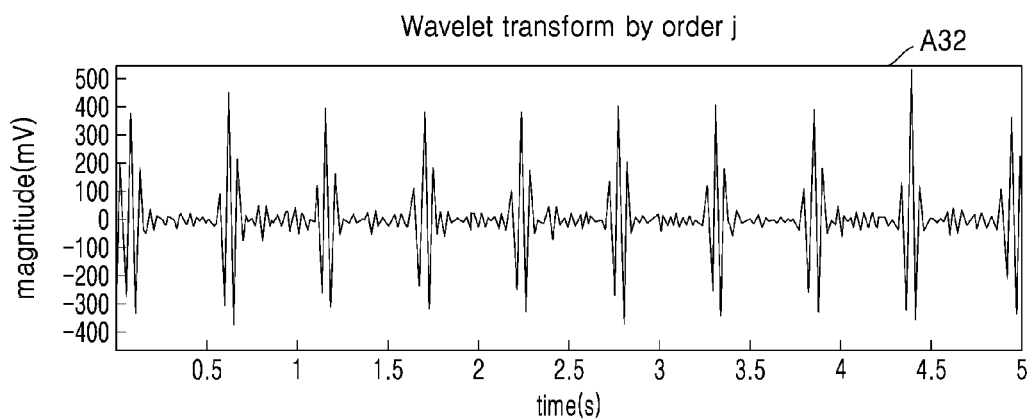
FIG. 6B is a diagram of a second transformed signal in a j-level according to one or more embodiments.
Figure 6C:
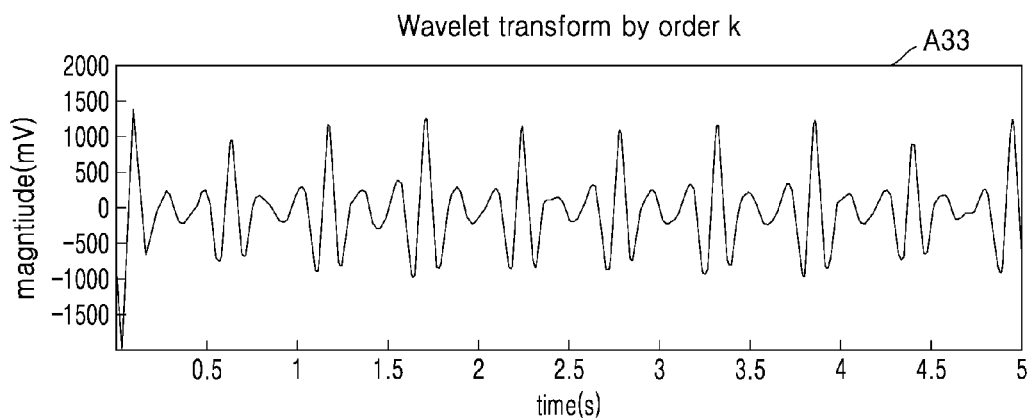
FIG. 6C is a diagram of a third transformed signal in a k-level according to one or more embodiments.

FIG. 6A is a diagram of first transformed signal in an i-level according to one or more embodiments. FIG. 6B is a diagram of second transformed signal in a j-level according to one or more embodiments. FIG. 6C is a diagram of third transformed signal in a k-level according to one or more embodiments.

The bio-signal measurement apparatus 100 may generate a first transformed signal A31, a second transformed signal A32, and a third transformed signal A33 by wavelet transforming the preprocessed electrocardiogram signal into three levels. In this case, the first transformed signal A31 may wavelet transform the preprocessed signal in an i-level manner. The second transformed signal A32 may wavelet transform the preprocessed signal in the j level manner. The third transformed signal A33 may wavelet transform the pre-processed signal in a k level manner.

Figure 7A:
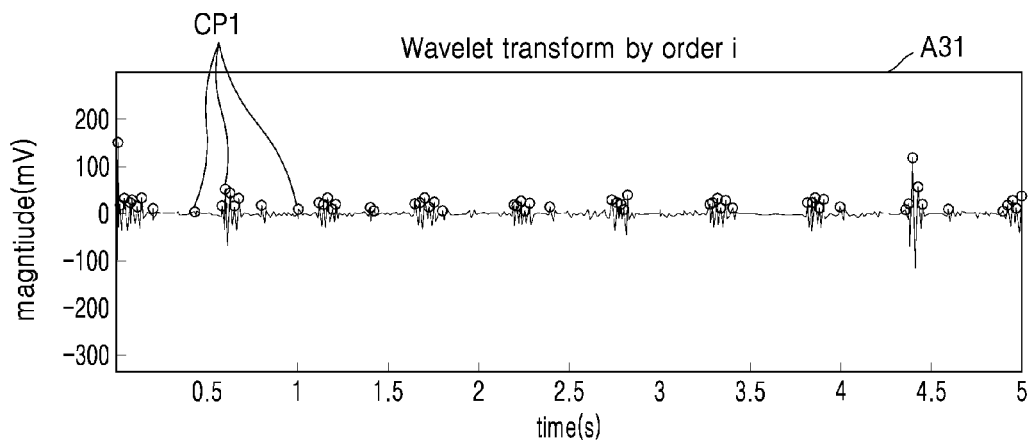
FIG. 7A is a diagram of candidate peak(s) detected from the first transformed signal according to one or more embodiments.
Figure 7B:
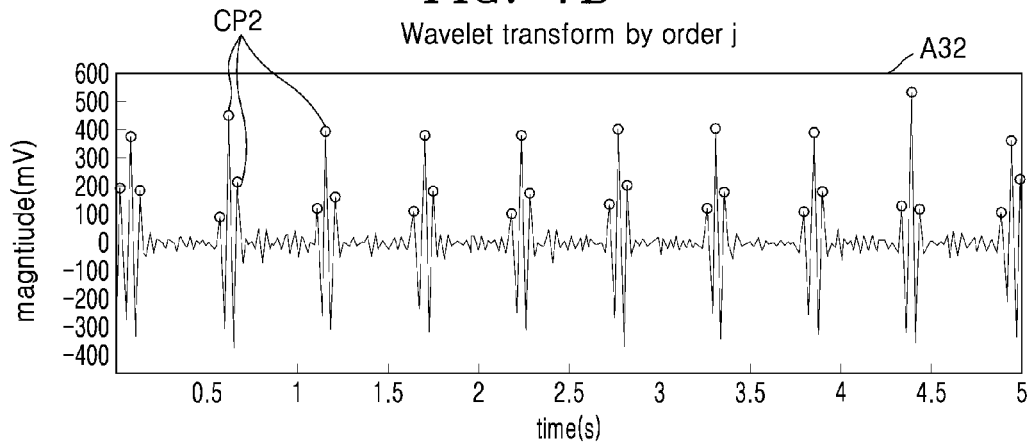
FIG. 7B is a diagram of candidate peak(s) detected from the second transformed signal according to one or more embodiments.
Figure 7C:
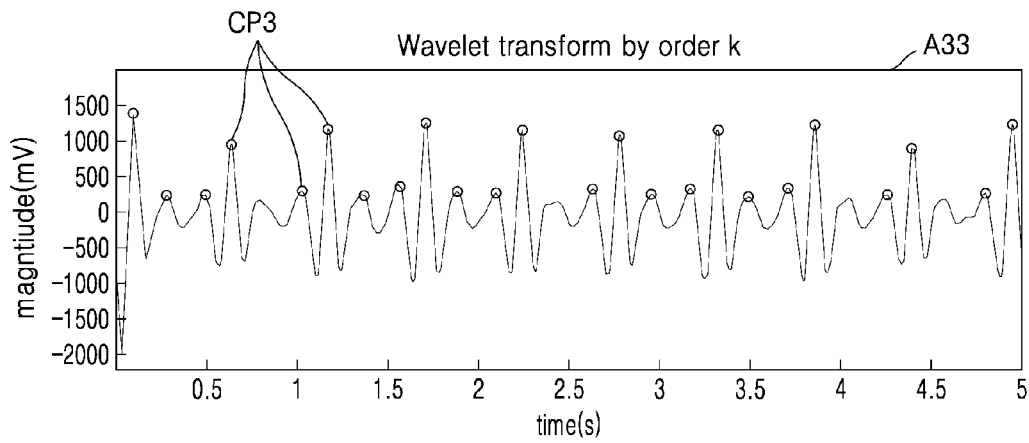
FIG. 7C is a diagram of candidate peak(s) detected from the third transformed signal according to one or more embodiments.

FIG. 7A is a diagram of candidate peak detected from the first transformed signal according to one or more embodiments. FIG. 7B is a diagram of candidate peak detected from the second transformed signal according to one or more embodiments. FIG. 7C is a diagram of candidate peak detected from the third transformed signal according to one or more embodiments.

The biosignal measurement apparatus 100 may detect candidate peaks CP1 in the first transformed signal A31 through a peak detection algorithm. In FIG. 7A, some peaks of A31 are assigned as CP1, but the remaining peaks also belong to CP1.

The bio-signal measurement apparatus 100 may detect candidate peaks CP2 in the second transformed signal A32 through a peak detection algorithm. In FIG. 7B, some peaks of A32 are assigned as CP2, but the remaining peaks also belong to CP2.

The bio-signal measurement apparatus 100 may detect candidate peaks CP3 from the third transformed signal A33 through a peak detection algorithm. In FIG. 7C, some peaks of A33 are assigned as CP3, but the remaining peaks also belong to CP3.

Figure 8A:
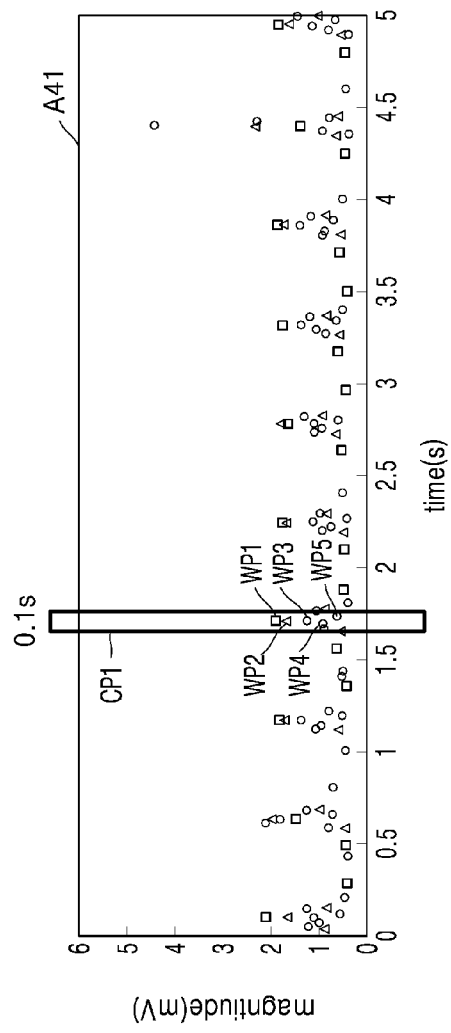
FIG. 8A is a diagram of candidate peaks in the window according to one or more embodiments.
Figure 8B:
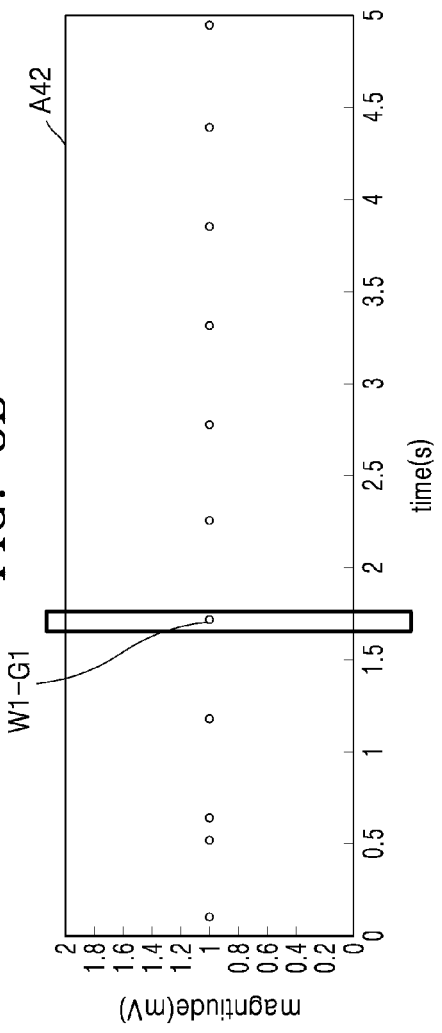
FIG. 8B is a diagram illustrating a process of calculating an average peak time value according to one or more embodiments.

FIG. 8A is a diagram of candidate peaks in the window according to one or more embodiments. FIG. 8B is a diagram illustrating a process of calculating an average peak time value according to one or more embodiments.

The bio-signal measurement apparatus 100 may generate one integrated data A41 including a first candidate peak, a second candidate peak, and a third candidate peak.

The bio-signal measurement apparatus 100 defines a window W1 having a time interval determined in A41, extracts candidate peaks WP1, WP2, WP3, Wp4, WP5 included in the window W1, and extracts the candidate peaks. The average value of the time values of (WP1, WP2, WP3, WP4, WP5) may be set as the average peak time value, and W1-G1 having the average peak time value may be extracted.

Figure 9:
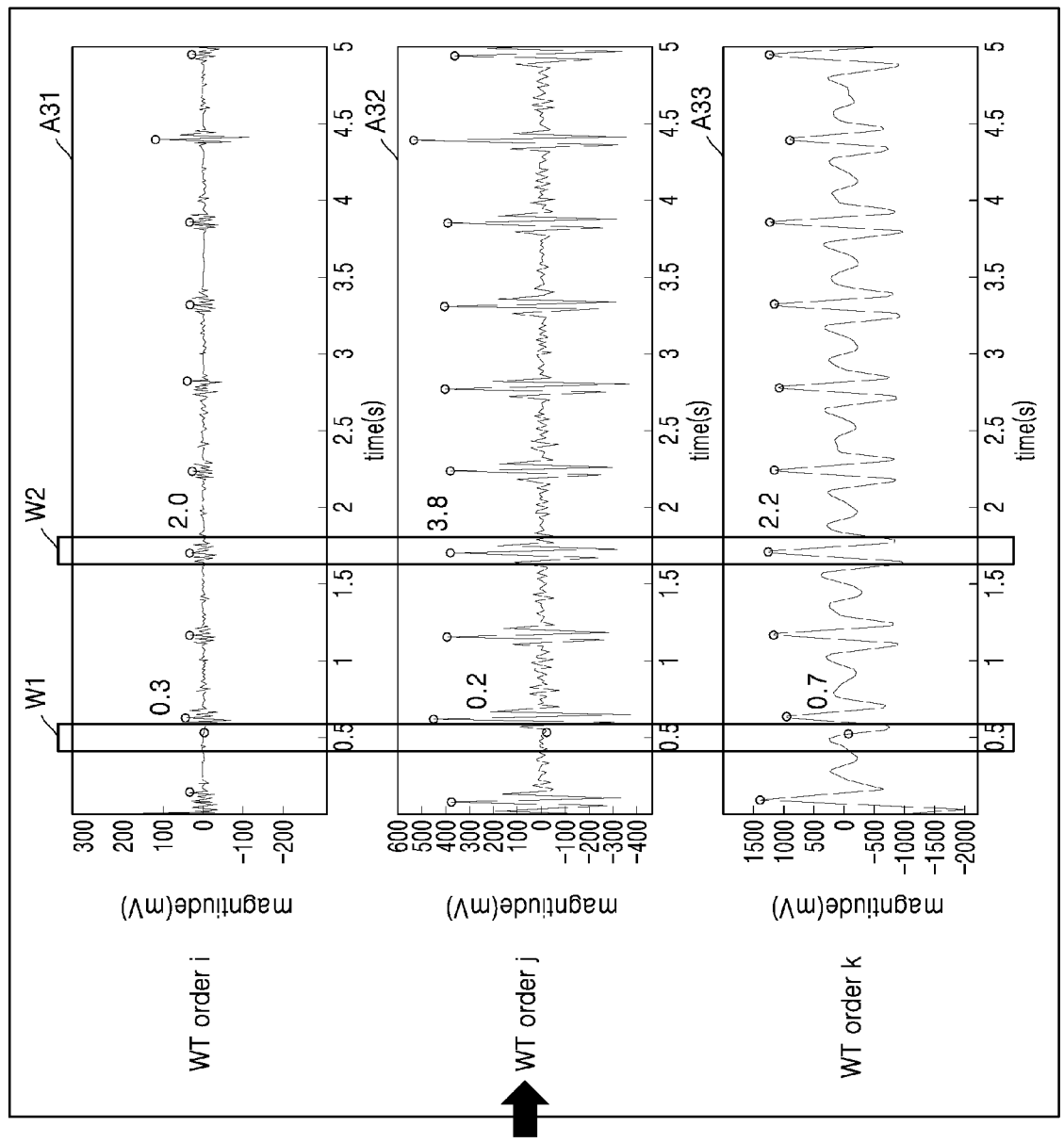
FIG. 9 is a diagram illustrating a process of calculating a complexity value according to one or more embodiments.

FIG. 9 is a diagram illustrating a process of calculating a complexity value according to one or more embodiments.

The bio-signal measurement apparatus 100' applies the windows W1 and W2 including the average peak time value to the first converted signal A31, the second transformed signal A32, and the third transformed signal A33, and calculate the complexity value within the windows.

Figure 10:
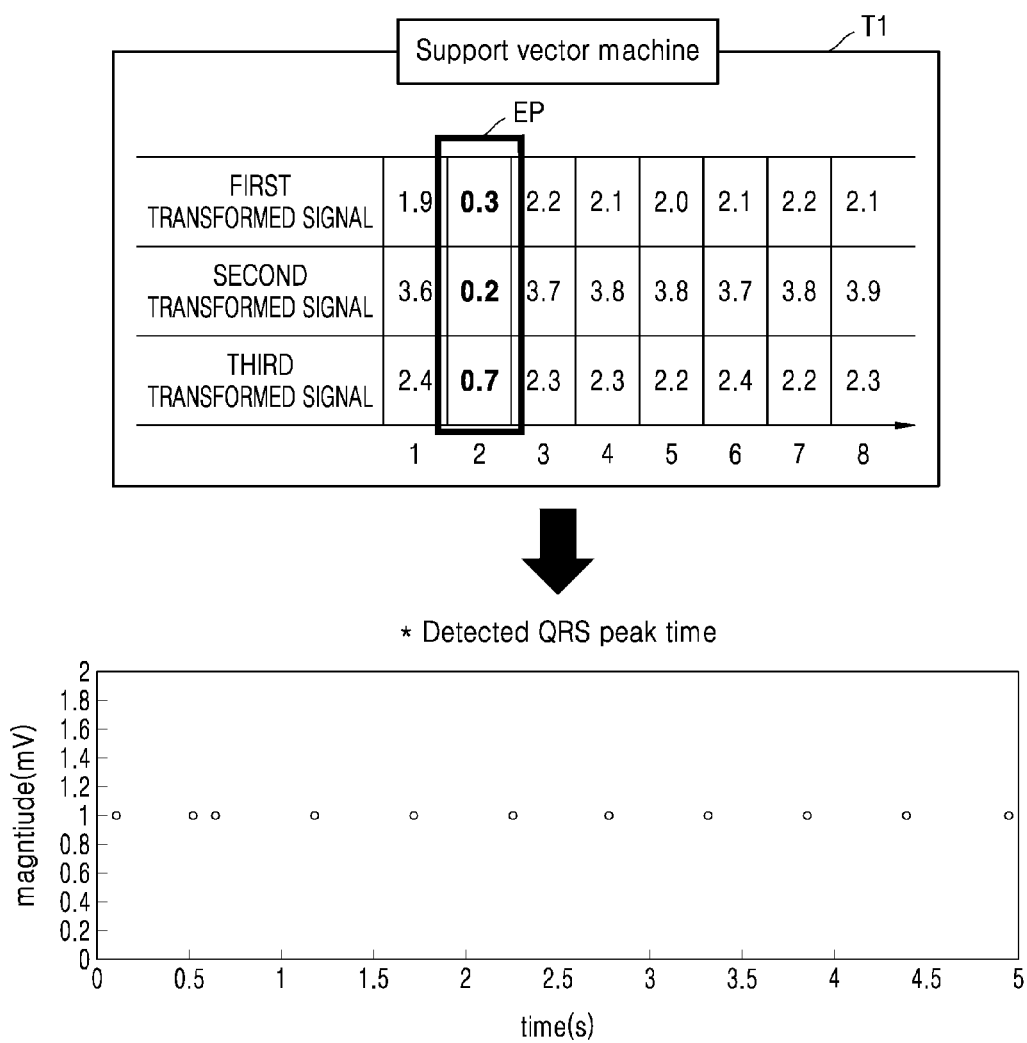
FIG. 10 is an exemplary diagram of complexity values calculated according to one or more embodiments.

FIG. 10 is an exemplary diagram of complexity values calculated according to one or more embodiments.

Complexity values calculated from the first to third converted signals may be generated as shown in the table T1. The complexity values in the second window are respectively calculated as 0.3, 0.2, and 0.7 in the first to third converted signals, and are less than a preset threshold complexity level, and the average peak time value of the second window cannot be the effective peak time value.

Complexity values in windows other than the second window may be equal to or greater than a critical complexity level, and an average peak time value may be an effective peak time value.

The apparatus described above may be implemented as a hardware component, a software component, and/or a combination of hardware components and software components. For example, the devices and components described in the embodiments may be implemented by using one or more general purpose or special purpose computers, such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. A processing device may execute an operating system (OS) and one or more software applications running on the OS. The processing device may also access, store, manipulate, process, and generate data in response to execution of software. For the convenience of explanation, it has been described above that one processing device is used. However, it would be obvious to one of ordinary skill in the art that the processing device may include a plurality of processing elements and/or a plurality of types of processing elements. For example, the processing device may include a plurality of processors or one processor and one controller. Also, other processing configurations like parallel processors may be employed.

The software may include a computer program, code, instructions, or a combination of one or more of the foregoing, to configure the processing device to operate as demanded or to command the processing device independently or collectively. For the purpose of interpreting or providing instructions or data to the processing device, software and/or data may be permanently or temporarily embodied in any type of machine, component, physical device, virtual equipment, computer storage medium, or a signal wave to be transmitted. The software may be distributed over networked computer systems so that they may be stored or executed in a distributed manner. The software and data may be stored on one or more computer-readable recording media.

The methods according to embodiments may be embodied in the form of program instructions that can be executed by various computer means and recorded on a computer-readable recording medium. The computer-readable recording media may include program instructions, data files, and data structures alone or a combination thereof. The program commands recorded on the medium may be specially designed and configured for example embodiments or may be published and available to one of ordinary skill in computer software. Examples of the computer-readable recording medium include a hardware device specially configured to store and perform program instructions, for example, a magnetic medium, such as a hard disk, a floppy disk, and a magnetic tape, an optical recording medium, such as a CD-ROM, a DVD, and the like, a magneto-optical medium, such as a floptical disc, ROM, RAM, a flash memory, and the like. Examples of program commands include machine language code such as code generated by a compiler, as well as high-level language code that may be executed by a computer using an interpreter or the like. The hardware device described above may be configured to operate as one or more software modules to perform the operations of the embodiments, and vice versa.

According to one or more embodiments, a signal peak may be detected by using complexity values of signals around a peak.

Also, according to one or more embodiments, a signal peak of a time period having a complexity value exceeding a critical complexity level determined by a machine learning or artificial intelligence algorithm may be detected.

Although the embodiments have been described by the limited embodiments and the drawings as described above, various modifications and variations are possible to one of ordinary skill in the art from the above description. For example, the described techniques may be performed in a different order than the described method, and/or components of the described systems, structures, devices, circuits, etc. may be combined or combined in a different manner than the described method, or other components. Or even if replaced or substituted by equivalents, an appropriate result can be achieved.

Therefore, other implementations, other embodiments, and equivalents of the claims fall within the scope of the claims to be described later.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A bio-signal measurement apparatus comprising:
   a bio-signal sensing circuit configured to sense an electrocardiogram signal using an electrode attached to a body;
   a processor;
   a memory that stores executable instructions that, when executed by the processor of the bio-signal measurement apparatus, facilitate performance of operations, the operations comprising:
   converting the electrocardiogram signal to a first transform signal by performing first-level wavelet transform;
   converting the electrocardiogram signal to a second transform signal by performing second-level wavelet transform;
   detecting first candidate peaks based on a magnitude of the first transform signal and detecting second candidate peaks based on a magnitude of the second transform signal;
   calculating an average value of time values of the first candidate peaks and the second candidate peaks included in a first window having a predetermined time interval based on a heart rate or an R-R interval and setting the average value of time values as a first average peak time value in the first window;
   calculating a first complexity value of the first transform signal and a second complexity value of the second transform signal for the first window including the first average peak time value, using a complexity calculation algorithm based on a turning point ratio (TPR), wherein the first complexity value and the second complexity value become higher as a number of turning points in the first window is greater, and the TPR corresponds to a value indicating a ratio of a location of a turning point indicating a change in magnitude of two adjacent pieces of data at a particular time point with respect to a total data length, and the turning point refers to a point at which a direction of data values is changed;
   determining the first average peak time value as a peak occurring time value when the first complexity value and the second complexity value exceed a pre-set critical complexity level; and
   detecting effective peaks in the electrocardiogram signal as peaks occurring at the peak occurring time value; and
   wherein the first-level wavelet transform is performed in an order different from an order applied to the second-level wavelet transform, and
   the order applied to the first-level wavelet transform and the order applied to the second-level wavelet transform are a changeable value.

2. The bio-signal measurement apparatus of claim 1, wherein the pre-set critical complexity level is a value determined based on a complexity value of a pre-processed electrocardiogram signal within time periods including R peaks designated in the electrocardiogram signal.

3. The bio-signal measurement apparatus of claim 1, wherein the processor is implemented so as not to calculate the first average peak time value corresponding to the first window when there is no candidate peak included in the first window.

4. A method comprising:
   sensing, by a bio-signal measurement apparatus using a bio-signal sensing circuit, an electrocardiogram signal by using an electrode attached to a body;
   converting the electrocardiogram signal to a first transform signal by performing a first-level wavelet transform and generating the first transform signal;
   converting the electrocardiogram signal to a second transform signal by performing a second-level wavelet transform and generating the second transform signal;
   detecting first candidate peaks based on a size of data with respect to the first transform signal and detecting second candidate peaks based on a size of data with respect to the second transform signal;
   calculating an average value of time values of the first candidate peaks and the second candidate peaks included in a first window having a predetermined time interval based on a heart rate or an R-R interval and setting the average value of time values as a first average peak time value in the first window;
   calculating a first complexity value of the first transform signal and a second complexity value of the second transform signal for the first window including the first average peak time value, using a complexity calculation algorithm based on a turning point ratio (TPR), wherein the first complexity value and the second complexity value become higher as a number of turning points in the first window is greater, and the TPR corresponds to a value indicating a ratio of a location of a turning point indicating a change in magnitude of two adjacent pieces of data at a particular time point with respect to a total data length, and the turning point refers to a point at which a direction of data values is changed;
   determining the first average peak time value as a peak occurring time value when the first complexity value and the second complexity value exceed a pre-set critical complexity level; and detecting effective peaks in the electrocardiogram signal as peaks occurring at the peak occurring time value; and wherein the first-level wavelet transform is performed in an order different from an order applied to the second-level wavelet transform, and the order applied to the first-level wavelet transform and the order applied to the second-level wavelet transform are a changeable value.

5. The method of claim 4, wherein the pre-set critical complexity level is a value determined based on a complexity value of a pre-processed electrocardiogram signal within time periods including R peaks designated in measured electrocardiogram signals.

6. The method of claim 4, further comprising calculating no average peak time value corresponding to the first window when there is no candidate peak included in the first window.

7. A non-transitory computer-readable recording medium storing one or more software for execution by a processor of a bio-signal measurement apparatus, the one or more software including instructions for:

sensing an electrocardiogram signal by using an electrode attached to a body using a bio-signal sensing circuit;

generating a first transform signal by first-level wavelet transforming the electrocardiogram signal;

generating a second transform signal by second-level wavelet transforming the electrocardiogram signal;

detecting first candidate peaks based on a size of data with respect to the first transform signal and detecting second candidate peaks based on a size of data with respect to the second transform signal;

calculating an average value of time values of the first candidate peaks and the second candidate peaks included in a first window having a predetermined time interval based on a heart rate or an R-R interval and setting the average value of time values as a first average peak time value in the first window;

calculating a first complexity value of the first transform signal and a second complexity value of the second transform signal for the first window including the first average peak time value using a complexity calculation algorithm based on a turning point ratio (TPR), wherein the first complexity value and the second complexity value become higher as a number of turning points in the first window is greater, and the TPR corresponds to a value indicating a ratio of a location of a turning point indicating a change in magnitude of two adjacent pieces of data at a particular time point with respect to a total data length, and the turning point refers to a point at which a direction of data values is changed;

determining the first average peak time value as a peak occurring time value when the first complexity value and the second complexity value exceed a pre-set critical complexity level; and detecting effective peaks in the electrocardiogram signal as peaks occurring at the peak occurring time value; and wherein the first-level wavelet transform is performed in an order different from an order applied to the second-level wavelet transform, and the order applied to the first-level wavelet transform and the order applied to the second-level wavelet transform are a changeable value.

* * * * *